US00PP27486P2

(12) United States Plant Patent
Rijk

(10) Patent No.: US PP27,486 P2
(45) Date of Patent: Dec. 20, 2016

(54) ***BEGONIA* PLANT NAMED 'FIUNUPWHIMP'**

(50) Latin Name: *Begonia hybrida*
Varietal Denomination: Fiunupwhimp

(71) Applicant: Nadine Rijk, De Lier (NL)

(72) Inventor: Nadine Rijk, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 14/545,697

(22) Filed: Jun. 6, 2015

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'Fiunupwhimp', characterized by its upright to spreading and mounded plant habit; relatively compact habit; freely basal branching habit; dark bronze-colored leaves; freely and continuously flowering habit; and single-type flowers that are white in color.

1 Drawing Sheet

Botanical designation: *Begonia hybrida.*
Cultivar denomination: 'FIUNUPWHIMP'.

BACKGROUND OF THE INVENTION

The present invention relates to a new and distinct cultivar of *Begonia* plant, botanically known as *Begonia hybrida*, and hereinafter referred to by the name 'Fiunupwhimp'.

The new *Begonia* plant is a product of a planned breeding program conducted by the Inventor in Aalsmeer, The Netherlands. The objective of the breeding program was to develop new compact and uniform *Begonia* plants with dark-colored leaves and single-type flowers.

The new *Begonia* plant originated from a cross-pollination made by the Inventor in 2011 of a proprietary selection of *Begonia hybrida* identified as code number 208193-002, not patented, as the female, or seed, parent and a proprietary selection of *Begonia hybrida* identified as code number 2314, not patented, as the male, or pollen, parent. The new *Begonia* plant was discovered and selected by the Inventor as a single flowering plant from within the progeny of the stated cross-pollination in a controlled greenhouse environment in Aalsmeer, The Netherlands in 2011.

Asexual reproduction of the new *Begonia* plant by vegetative tip cuttings in a controlled greenhouse environment in Aalsmeer, The Netherlands since 2011 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Fiunupwhimp'. These characteristics in combination distinguish 'Fiunupwhimp' as a new and distinct *Begonia* plant:

1. Upright to spreading and mounded plant habit; relatively compact.
2. Freely basal branching habit.
3. Dark bronze-colored leaves.
4. Freely and continuously flowering habit.
5. Single-type flowers that are white in color.

Plants of the new *Begonia* can be compared to plants of the proprietary parent selections. Plants of the new *Begonia* differ from plants of the parent selections in the following characteristics:

1. Plants of the new *Begonia* are more uniform than plants of the parent selections.
2. Leaves of plants of the new *Begonia* are darker in color than leaves of plants of the parent selections.
3. Plants of the new *Begonia* are more freely flowering than plants of the parent selections.

Plants of the new *Begonia* can be compared to plants of *Begonia hybrida* 'Fimissmo', disclosed in a U.S. Plant Patent application filed concurrently, 14/545,695. Plants of the new *Begonia* differ primarily from plants of 'Fimissmo' in the following characteristics:

1. Plants of the new *Begonia* have dark bronze-colored leaves whereas plants of 'Fimissmo' have dark green-colored leaves.
2. Plants of the new *Begonia* have smaller flowers than plants of 'Fimissmo'.
3. Plants of the new *Begonia* have single-type flowers whereas plants of 'Fimissmo' have double flowers.
4. Plants of the new *Begonia* have white-colored flowers whereas plants of 'Fimissmo' have cream-colored flowers with light pink-colored margins.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a side perspective view of a typical flowering plant of 'Fiunupwhimp' grown in a container.

DETAILED BOTANICAL DESCRIPTION

Plants used for the aforementioned photograph and following observations and measurements were grown in 12-cm containers during the summer in a glass-covered greenhouse in Rheinberg, Germany. During the production of the plants, day temperatures ranged from 17° C. to 30° C. and night temperatures ranged from 10° C. to 20° C. Plants were eight weeks old when the photograph and the description were taken. In the following description, color references are made to The Royal Horticultural Society Colour Chart, 2007 Edition, except where general terms of ordinary dictionary significance are used.

Botanical classification: *Begonia hybrida* 'Fiunupwhimp'.

Parentage:

*Female, or seed, parent*.—Proprietary selection of *Begonia hybrida* identified as code number 208193-002, not patented.

*Male, or pollen, parent*.—Proprietary selection of *Begonia hybrida* identified as code number 2314, not patented.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 22° C. to 30° C.

*Time to produce a rooted young plant, summer*.—About 25 days at temperatures about 22° C. to 30° C.

*Time to produce a rooted young plant, winter*.—About 28 days at temperatures about 20° C. to 25° C.

*Root description*.—Medium in thickness, fibrous; whitish grey in color; plants of the new *Begonia* have not been observed to form tubers.

*Rooting habit*.—Moderately freely branching; medium density.

Plant description:

*Plant form and growth habit*.—Upright to spreading and mounded plant habit; relatively compact; pendulous with development; freely basal branching with about four primary branches; moderately vigorous to vigorous growth habit.

*Plant height*.—About 37 cm.

*Plant width*.—About 30 cm.

*Lateral branch description*.—Length: About 28 cm to 36 cm. Diameter: About 1 cm to 4 cm. Internode length: About 8 mm to 10 mm. Texture: Smooth, glabrous. Color: Close to 174B.

*Leaf description*.—Arrangement: Alternate, simple. Length: About 11 cm to 19 cm. Width: About 5 cm to 6 cm. Shape: Ovate to lanceolate. Apex: Acute. Base: Cordate. Margin: Serrate. Texture, upper and lower surfaces: Smooth, glabrous. Venation pattern: Palmate; reticulate. Color: Developing and fully expanded leaves, upper surface: Close to 200A; venation, close to 143A. Developing and fully expanded leaves, lower surface: Close to 183A; venation, close to 183A. Petioles: Length: About 3 cm to 6 cm. Diameter: About 3 mm to 4 mm. Texture, upper and lower surfaces: Smooth, glabrous. Color, upper surface: Close to 183C. Color, lower surface: Close to 176C.

Flower description:

*Flowering habit*.—Single-type flowers arranged in axillary cymes; freely flowering habit with numerous flowers developing per plant; flowers pendulous and face outwardly to downwardly.

*Fragrance*.—None detected.

*Natural flowering season*.—Plants in full flower about eight weeks after planting; long flowering period, in the garden plants flower freely and continuously throughout the summer in Northern Europe and can be flowered year-round in greenhouses.

*Flower longevity*.—Individual flowers last about four weeks on the plant; flowers persistent.

*Inflorescence height* (*including peduncle*).—About 14 cm to 15 cm.

*Inflorescence diameter*.—About 6 cm.

*Inflorescence peduncles*.—Length: About 7 cm to 9 cm. Diameter: About 2 mm to 3 mm. Angle: About 30° to 45° from vertical. Strength: Moderately strong. Texture: Smooth, glabrous. Color: Close to 174C.

*Female flower buds*.—Length: About 1 cm. Diameter: About 1 cm. Shape: Ovoid. Texture: Smooth, glabrous. Color: Close to 2D.

*Female flowers*.—Diameter: About 3 cm. Depth (height): About 1 cm.

*Female flower tepals*.—Quantity per flower and arrangement: Typically four per flower arranged in a single whorl. Length: About 2 cm to 3 cm. Width: About 1.5 cm to 2 cm. Shape: Ovate. Apex: Acute. Base: Cordate. Margin: Entire. Texture, upper and lower surfaces: Smooth, glabrous. Color: When opening and fully opened, upper surface: Close to NN155B; color does not change with development. When opening and fully opened, lower surface: Close to NN155B and 62B; color does not change with development.

*Female flower tepaloids*.—None observed.

*Female flower pedicels*.—Length: About 2.5 cm to 3 cm. Diameter: About 2 mm. Aspect: About 90° from peduncle axis. Strength: Moderately strong. Texture: Smooth, glabrous. Color: Close to 174C.

*Female flowers reproductive organs*.—Quantity of pistils per flower: Three. Pistil length: About 1.5 cm to 2 cm. Style length: About 5 mm. Style color: Close to 145A. Stigma shape: Curled. Stigma color: Close to 9A. Ovary color: Close to 145A. Fruits and seeds: Fruit and seed development have not been observed on plants of the new *Begonia*.

*Male flower buds*.—Length: About 3 cm. Diameter: About 2 cm to 2.5 cm. Shape: Ovoid. Texture: Smooth, glabrous. Color: Close to 2D.

*Male flowers*.—Diameter: About 6.5 cm. Depth (height): About 2.5 cm.

*Male flower tepals*.—Quantity per flower and arrangement: Typically about four per flower arranged in a single whorl. Length: About 2.5 cm to 4 cm. Width: About 2.5 cm to 3.5 cm. Shape: Ovate. Apex: Acute. Base: Cordate. Margin: Entire. Texture, upper and lower surfaces: Smooth, glabrous. Color: When opening and fully opened, upper surface: Close to NN155B; color does not change with development.

When opening and fully opened, lower surface: Close to NN155B and 62B; color does not change with development.

*Male flower tepaloids*.—None observed.

*Male flower pedicels*.—Length: About 1 cm to 2.5 cm. Diameter: About 2 mm to 4 mm. Aspect: About 90° from peduncle axis. Strength: Moderately strong. Texture: Smooth, glabrous. Color: Close to 174D.

*Male flowers reproductive organs*.—Quantity of stamens per flower: About 55. Anther length: About 2 mm. Anther shape: Oval. Anther color: Close to 9A. Pollen amount: Moderate. Pollen color: Close to 5C.

Disease & pest resistance: Resistance to pathogens and pests common to *Begonia* plants has not been observed on plants of the new *Begonia*.

Temperature tolerance: Plants of the new *Begonia* have been observed to tolerate temperatures ranging from about 4° C. to about 35° C.

It is claimed:

1. A new and distinct *Begonia* plant named 'Fiunup-whimp' as illustrated and described.

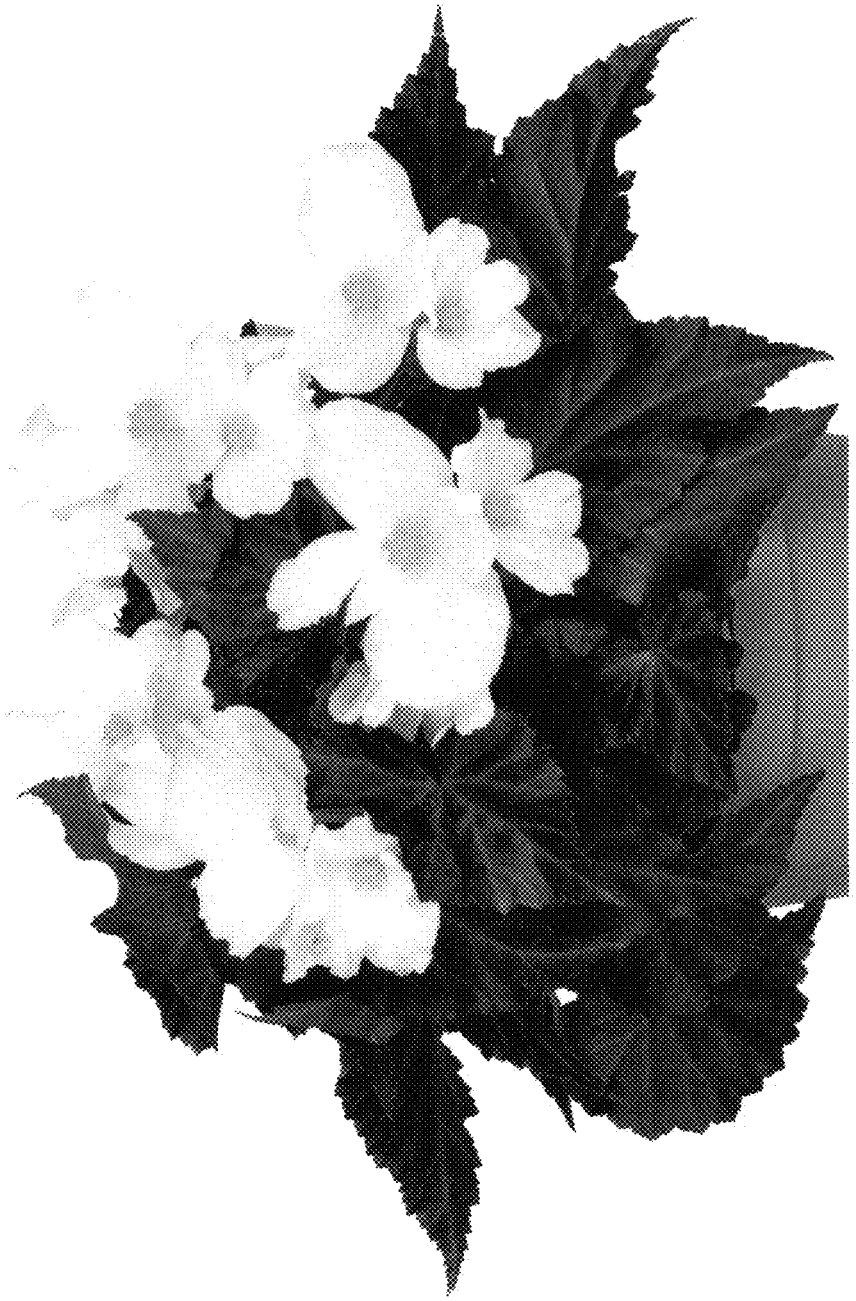

* * * * *